US009677037B2

(12) United States Patent
Mizoguchi

(10) Patent No.: US 9,677,037 B2
(45) Date of Patent: Jun. 13, 2017

(54) CELL CULTURE CARRIER AND CELL CULTURE VESSEL

(71) Applicant: FUJIFILM Corporation, Minato-Ku, Tokyo (JP)

(72) Inventor: Takao Mizoguchi, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 200 days.

(21) Appl. No.: 14/500,115

(22) Filed: Sep. 29, 2014

(65) Prior Publication Data

US 2015/0093827 A1    Apr. 2, 2015

(30) Foreign Application Priority Data

Sep. 30, 2013   (JP) ................. 2013-205584

(51) Int. Cl.
| | | |
|---|---|---|
| *C12N 5/00* | (2006.01) | |
| *C12M 1/12* | (2006.01) | |
| *B01D 69/02* | (2006.01) | |

(52) U.S. Cl.
CPC ............ *C12M 25/04* (2013.01); *B01D 69/02* (2013.01); *C12M 25/02* (2013.01); *C12N 5/0068* (2013.01); *B01D 2325/021* (2013.01)

(58) Field of Classification Search
None
See application file for complete search history.

(56) References Cited

U.S. PATENT DOCUMENTS

| | | | | |
|---|---|---|---|---|
| 4,889,631 A | * | 12/1989 | Rigby ................ | B01D 67/0065 210/493.1 |
| 4,963,490 A | * | 10/1990 | Churchouse ......... | C12N 5/0068 435/297.1 |

| | | | |
|---|---|---|---|
| 2007/0029256 A1 | | 2/2007 | Nakano et al. |
| 2007/0235342 A1 | * | 10/2007 | Matsuo ................. B82Y 20/00 205/175 |
| 2008/0153125 A1 | | 6/2008 | Buttry et al. |
| 2013/0210131 A1 | | 8/2013 | Renken |

FOREIGN PATENT DOCUMENTS

| | | |
|---|---|---|
| EP | 0363123 A1 | 4/1990 |
| JP | 10295369 A | 11/1998 |
| JP | 2008238048 A | 10/2008 |
| JP | 2009254271 A | 11/2009 |
| JP | 2010-226975 A | 10/2010 |
| JP | 2012213390 A | 11/2012 |
| WO | 2005014149 A1 | 2/2005 |

OTHER PUBLICATIONS

Communication, dated Jan. 28, 2015, issued in corresponding EP Application No. 14187015.4, 6 pages in English.
Ingham et al., "Where bio meets nano: The many uses for nanoporous aluminum oxide in biotechnology," Biotechnology Advances, vol. 30, No. 5, Sep. 1, 2012, pp. 1089-1099, XP55163479.
Communication dated Apr. 26, 2016, from the Japanese Patent Office in counterpart application No. 2013-205584.

* cited by examiner

*Primary Examiner* — Robert Yamasaki
(74) *Attorney, Agent, or Firm* — Sughrue Mion, PLLC

(57) ABSTRACT

A cell culture carrier comprises an anodic oxide film having a plurality of micropores penetrating in a thickness direction from a front surface to a rear surface, wherein an average opening diameter A of a front surface-side opening portion of the plurality of micropores and an average opening diameter B of a rear surface-side opening portion thereof have different values from each other, and the plurality of micropores has a shape in which an average diameter increases or decreases toward the rear surface-side opening portion from the front surface-side opening portion.

13 Claims, 5 Drawing Sheets

CELL CULTURE CARRIER AND CELL CULTURE VESSEL

CROSS-REFERENCE TO RELATED APPLICATIONS

The present application claims priority under 35 U.S.C. §119 to Japanese Patent Application No. 2013-205584, filed on Sep. 30, 2013. Each of the above application(s) is hereby expressly incorporated by reference, in its entirety, into the present application.

BACKGROUND OF THE INVENTION

This invention relates to a cell culture carrier and a cell culture vessel. Particularly, this invention relates to a cell culture carrier and a cell culture vessel that use an anodic oxide film having a plurality of micropores.

In recent years, as cell culture technologies have advanced, various cell culture carriers for accelerating growth of cells are being developed. A cell culture carrier is generally placed in a culture chamber accommodating a cell culture medium in a cell culture vessel so as to accelerate growth of cells having adhered to the surface of the carrier, thereby maintaining cell viability at a high level.

As such a cell culture carrier, there is a cell culture carrier configured with an anodic oxide film having a plurality of micropores penetrating the film in the thickness direction. For example, JP 2010-226975 A discloses a "membrane for culturing cells (cell culture carrier) having an inorganic material on the surface and/or inside micropores of an anodized oxide film of aluminum" (claim 1).

As a result of culturing cells by using the cell culture carrier described in JP 2010-226975 A, the inventors of this invention clearly ascertained that the cell viability can be further improved.

SUMMARY OF THE INVENTION

An object of this invention is to provide a cell culture carrier and a cell culture vessel that can greatly improve cell viability.

In order to achieve the above object, the inventors of this invention conducted thorough research. As a result, they found that when a plurality of micropores penetrating a cell culture carrier has a predetermined shape, cell viability is greatly improved, and based on this finding, they completed this invention.

That is, this invention provides a cell culture carrier and a cell culture vessel configured as below.

(1) A cell culture carrier comprising an anodic oxide film having a plurality of micropores penetrating in a thickness direction from a front surface to a rear surface, wherein an average opening diameter A of a front surface-side opening portion of the plurality of micropores and an average opening diameter B of a rear surface-side opening portion thereof have different values from each other, and the plurality of micropores has a shape in which an average diameter increases or decreases toward the rear surface-side opening portion from the front surface-side opening portion.

(2) The cell culture carrier according to (1), wherein the plurality of micropores has a shape in which the average diameter gradually increases or decreases toward the rear surface-side opening portion from the front surface-side opening portion.

(3) The cell culture carrier according to (1), wherein the plurality of micropores has a shape in which the average diameter increases stepwise or decreases stepwise toward the rear surface-side opening portion from the front surface-side opening portion.

(4) The cell culture carrier according to any one of (1) to (3), wherein a value of a larger one of the average opening diameter A and the average opening diameter B is 1.05 to 10.0 times a value of a smaller one thereof.

(5) The cell culture carrier according to any one of (1) to (4), wherein a smaller one of the average opening diameter A and the average opening diameter B is 40 nm to 80 nm.

(6) The cell culture carrier according to any one of (1) to (5), wherein a larger one of the average opening diameter A and the average opening diameter B is 65 nm to 100 nm.

(7) The cell culture carrier according to any one of (1) to (6), wherein an opening ratio of a surface of the front surface and the rear surface which has a smaller one of the average opening diameter A and the average opening diameter B is equal to or greater than 20%.

(8) The cell culture carrier according to (7), wherein an average opening ratio of both the front surface and the rear surface is equal to or greater than 51%.

(9) The cell culture carrier according to any one of (1) to (8), wherein a thickness of the cell culture carrier is 10 μm to 300 μm.

(10) A cell culture vessel comprising: at least one culture well having a culture chamber accommodating a cell culture medium; and the cell culture carrier according to any one of (1) to (9) that has a front surface to which cells adhere and which is positioned inside the culture chamber, and that is disposed such that the cell culture medium fills the cell culture carrier from the front surface to the rear surface of the cell culture carrier.

(11) The cell culture vessel according to (10), wherein the cell culture carrier is disposed such that the front surface and the rear surface thereof are positioned inside the culture chamber.

(12) The cell culture vessel according to (10), further comprising an accommodation portion that has an accommodation chamber accommodating the cell culture medium in an amount greater than that of the cell culture medium accommodated in the culture chamber, wherein the cell culture carrier configures at least a bottom plate of the culture well, the bottom plate of the culture well is disposed so as to be positioned inside the accommodation chamber, and the culture chamber is in communication with the accommodation chamber through the plurality of micropores.

(13) The cell culture vessel according to (12), wherein the culture well has an expansion portion that is in the form of a flat plate extending toward a side portion of the accommodation portion from a side edge of the bottom plate, and the accommodation portion has a supporter that supports the expansion portion in the side portion thereof.

(14) The cell culture vessel according to (13), wherein the expansion portion is formed of another anodic oxide film having a plurality of micropores penetrating the another anodic oxide film in a thickness direction and integrally formed with the cell culture carrier.

According to this invention, it is possible to provide a cell culture carrier and a cell culture vessel that can greatly improve cell viability.

DETAILED DESCRIPTION OF THE INVENTION

Hereinafter, the cell culture carrier and the cell culture vessel of this invention will be described in detail.

The cell culture carrier of this invention is a cell culture carrier formed of an anodic oxide film having a plurality of micropores penetrating therethrough in the thickness direction from the front surface to the rear surface, in which the average opening diameter A of the front surface-side opening portion of the plurality of micropores and the average opening diameter B of the rear surface-side opening portion thereof are different values from each other, and the plurality of micropores has a shape in which an average diameter increases or decreases toward the rear surface-side opening portion from the front surface-side opening portion.

Next, the cell culture carrier of this invention will be described using FIG. 1.

Figure 1A:
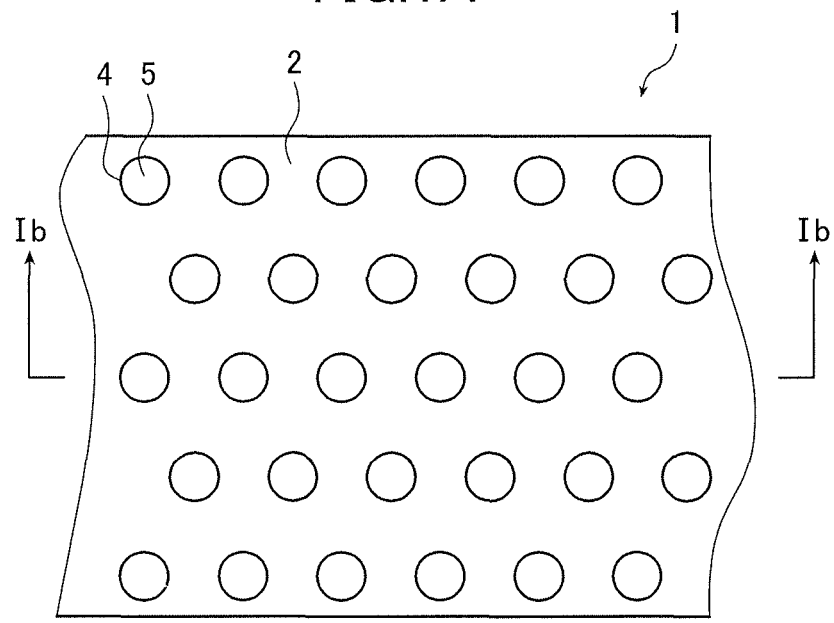
FIG. 1A is a front view showing an example of a preferable embodiment of the cell culture carrier of this invention.
Figure 1B:
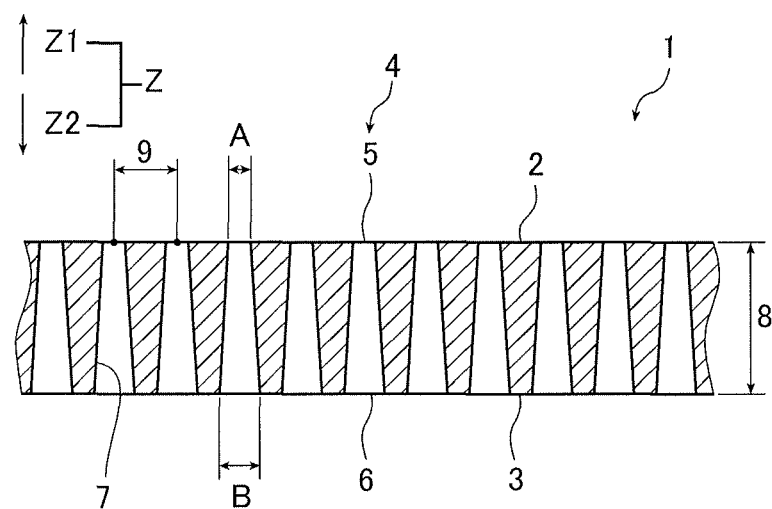
FIG. 1B is a cross-sectional view taken along line Ib-Ib of FIG. 1A.

FIG. 1 is a simplified view showing an example of a preferable embodiment of the cell culture carrier of this invention. FIG. 1A is a front view, and FIG. 1B is a cross-sectional view taken along line Ib-Ib of FIG. 1A.

A cell culture carrier 1 of this invention has a plurality of micropores 4 penetrating in a thickness direction Z from a front surface 2 to a rear surface 3. The plurality of micropores 4 has a front surface-side opening portion 5 and a rear surface-side opening portion 6, and is formed such that the value of the average opening diameter A of the front surface-side opening portion 5 is smaller than the value of the average opening diameter B of the rear surface-side opening portion 6. In addition, the front surface-side opening portion 5 and the rear surface-side opening portion 6 are connected to each other by an inner peripheral surface 7 of the cell culture carrier 1 which inclines smoothly so as to increase in diameter toward the rear surface-side opening portion 6. Thus, the plurality of micropores 4 has a shape in which the average diameter gradually increases toward the rear surface-side opening portion 6 from the front surface-side opening portion 5.

Figure 2:
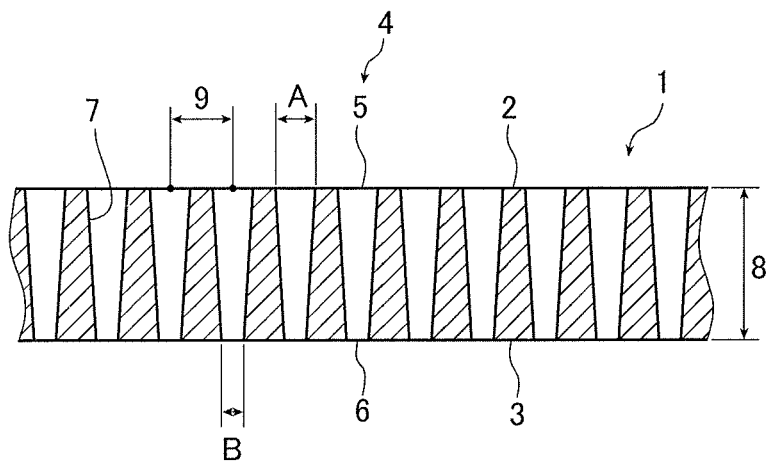
FIG. 2 is a cross-sectional view showing a modification example of the cell culture carrier of this invention.

In addition, the cell culture carrier 1 of this invention, as shown in FIG. 2, can also be formed such that the value of the average opening diameter A of the front surface-side opening portion 5 of the plurality of micropores 4 is greater than the value of the average opening diameter B of the rear surface-side opening portion 6 thereof. The front surface-side opening portion 5 and the rear surface-side opening portion 6 are connected to each other by the inner peripheral surface 7 of the cell culture carrier 1 which inclines smoothly so as to decrease in diameter toward the rear surface-side opening portion 6. Thus, the plurality of micropores 4 is formed such that the average diameter gradually decreases toward the rear surface-side opening portion 6 from the front surface-side opening portion 5.

In addition, in the cell culture carrier of this invention, the plurality of micropores can also have a shape in which the average diameter increases stepwise or decreases stepwise toward the rear surface-side opening portion from the front surface-side opening portion.

Figure 3:
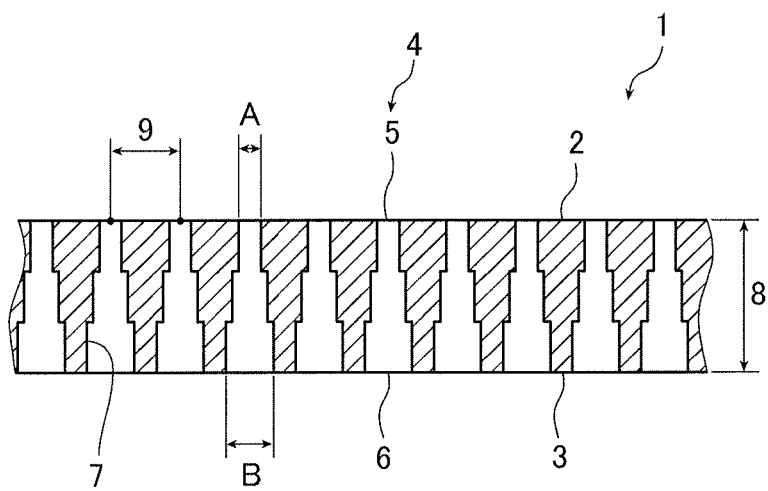
FIG. 3 is a cross-sectional view showing another modification example of the cell culture carrier of this invention.

For example, as shown in FIG. 3, the plurality of micropores is formed such that the value of the average opening diameter A of the front surface-side opening portion 5 is smaller than the value of the average opening diameter B of the rear surface-side opening portion 6, and the front surface-side opening portion 5 and the rear surface-side opening portion 6 can be connected to each other by the inner peripheral surface 7 of the cell culture carrier 1 which increases stepwise in diameter toward the rear surface-side opening portion 6. Thus, the plurality of micropores 4 is formed such that the average diameter increases stepwise toward the rear surface-side opening portion 6 from the front surface-side opening portion 5.

In the cell culture carrier 1 of this invention, as described above, in order to greatly improve the viability of the cells, the plurality of micropores 4 has a shape in which the average diameter consistently increases or decreases toward the rear surface-side opening portion 6 from the front surface-side opening portion 5. That is, when the cell culture carrier 1 is disposed in a cell culture vessel described below, it is possible to allow a cell culture medium to smoothly flow between a front surface 2 side and a rear surface 3 side through the plurality of micropores 4, and it is possible to greatly improve the viability of the cells by circulating and changing the cell culture medium at the periphery of the cells cultured on the front surface 2.

In addition, in the cell culture carrier of this invention, since the cell culture medium is brought into contact with the cells which are cultured in a state of adhering on the front surface from not only the upper side but also the lower side, it is possible to supply a large amount of the cell culture medium, and thus, it is possible to improve the viability of the cells.

In order to allow the cell culture medium to more smoothly flow, as shown in FIGS. 1 and 2, it is preferable for the plurality of micropores to have a shape in which the average diameter thereof gradually increases or decreases toward the rear surface-side opening portion 6 from the front surface-side opening portion 5.

In addition, in order to prevent the front surface-side opening portion 5 from hindering growth of the cells cultured on the front surface 2, as shown in FIG. 1, it is more preferable for the plurality of micropores 4 to have a shape in which the average diameter thereof gradually increases toward the rear surface-side opening portion 6 from the front surface-side opening portion 5, such that the average opening diameter A of the front surface-side opening portion 5 is further reduced.

Next, the material, dimension, formation, and the like of the cell culture carrier of this invention will be described in detail.

In this invention, between the average opening diameter A of the front surface-side opening portion of the plurality of micropores and the average opening diameter B of the rear surface-side opening portion thereof, the larger average opening diameter is greater than the smaller average opening diameter, preferably by 1.05-fold to 10.0-fold, more preferably by 1.1-fold to 4.5-fold, and even more preferably by 1.15-fold to 3.0-fold.

If the ratio between the average opening diameter A and the average opening diameter B is within the above range, it is possible to allow the cell culture medium to more smoothly flow between the front surface side and the rear surface side of the cell culture carrier through the plurality of micropores and to further improve the cell viability.

Moreover, between the average opening diameter A of the front surface-side opening portion of the plurality of micropores and the average opening diameter B of the rear surface-side opening portion thereof, the smaller average opening diameter is preferably from 40 nm to 80 nm.

Furthermore, between the average opening diameter A of the front surface-side opening portion of the plurality of micropores and the average opening diameter B of the rear surface-side opening portion thereof, the larger average opening diameter is preferably from 65 nm to 100 nm.

If the average opening diameter is within the above range, it is possible to allow the cell culture medium to more smoothly flow between the front surface side and the rear surface side of the cell culture carrier through the plurality of micropores and to further improve the cell viability. In addition, if the average opening diameter is within the above range, it is possible to inhibit growth of cells, which are cultured on the front surface of the cell culture carrier, from being hindered.

Herein, the average opening diameter is a value obtained by capturing images (20,000× magnification) of five sites of the surface of the cell culture carrier by FE-SEM, measuring an opening diameter of the respective micropores present in a field of view of 1 μm×1 μm in each of the images of surface, and calculating the average of the opening diameter of the micropores obtained from the images of five sites of the surface.

In addition, between the front surface and the rear surface of the cell culture carrier, the opening ratio of the surface showing a small average opening diameter is preferably equal to or greater than 20%, more preferably equal to or greater than 40%, and even more preferably equal to or greater than 51%. Further, between the front surface and the rear surface of the cell culture carrier, the opening ratio of the surface showing a large average opening diameter is preferably equal to or greater than 30%, more preferably equal to or greater than 40%, even more preferably equal to or greater than 60%, and particularly preferably equal to or greater than 70%. Moreover, the opening ratios of the front surface and the rear surface of the cell culture carrier are preferably equal to or less than 90%. Furthermore, the average opening ratio of both surfaces obtained when combining the front surface and the rear surface of the cell culture carrier is preferably equal to or greater than 30%, more preferably equal to or greater than 40%, even more preferably equal to or greater than 51%, and particularly preferably equal to or greater than 58%.

If the opening ratio of the cell culture carrier is set as described above, it is possible to allow the cell culture medium to smoothly flow between the front surface side and the rear surface side of the cell culture carrier through the plurality of micropores, and thus, it is possible to further improve the viability of the cells. In particular, if the average opening ratio of both surfaces is equal to or greater than 51%, the flow of the cell culture medium can be further promoted, and it is possible to significantly improve the viability of the cells.

Herein, the opening ratio of the front surface is represented by "area of the front surface opening portion/area of the front surface", and also the opening ratio of the rear surface is represented by "area of the rear surface opening portion/area of the rear surface". In addition, the average opening ratio of both surfaces can be represented by "(opening ratio of the front surface+opening ratio of the rear surface)/2". The area of the opening portion is obtained by a method in which images of the front surface and the rear surface of the cell culture carrier are captured by FE-SEM; for a field of view of 1 μm×1 μm in the obtained images, binarization is conducted using image analysis software or the like, and a micropore portion and a non-micropore portion are observed; and a geometrical area determined by a method of calculating an equivalent circle diameter of the micropore portion, that is, an area that is assumed to be a two-dimensional plane is calculated. In images which have been captured at five sites on each of the front surface and the rear surface, the area of the above-described opening portion is determined, and the average value of the opening ratios calculated from these values is taken as the opening ratio of the front surface and the opening ratio of the rear surface.

In order to further improve the flow of the cell culture medium, the average density of the plurality of micropores is preferably from 1 micropore/μm$^2$ to 15,000 micropores/μm$^2$, more preferably from 2 micropores/μm$^2$ to 1,000 micropores/μm$^2$, and even more preferably from 3 micropores/μm$^2$ to 300 micropores/μm$^2$.

Herein, the average density is a value obtained by capturing an image (20,000× magnification) of the front surface by FE-SEM, counting the number of micropores present in a field of view of 1 μm×1 μm in the image to obtain density of the micropores, and calculating the average of the thus obtained density for five sites of the field of view of 1 μm×1 μm.

In order to further improve the flow of the cell culture medium, the thickness (indicated by reference number 8 in FIG. 1B) of the cell culture carrier is preferably equal to or smaller than 300 μm, more preferably equal to or smaller than 200 μm, and even more preferably equal to or smaller than 150 μm.

Moreover, in order to further improve the flow of the cell culture medium, an aspect ratio (average length/average opening diameter) of the plurality of micropores is preferably equal to or lower than 5,000, more preferably equal to or lower than 3,000, and even more preferably equal to or lower than 2,000.

In addition, a center-to-center distance (portion indicated by reference number 9 in FIG. 1, also referred to as "pitch") between the respective micropores adjacent to each other is preferably 10 nm to 500 nm, more preferably 30 nm to 400 nm, and even more preferably 50 nm to 300 nm. If the pitch is within the above range, it is possible to arrange the plurality of micropores in a balanced manner, and to further improve the cell viability by evenly supplying the cell culture medium.

Herein, the center-to-center distance is a value obtained by capturing images (20,000× magnification) of five sites of the surface of the cell culture carrier by FE-SEM, measuring a distance between centers of the respective micropores present in a field of view of 1 μm×1 μm in each of the images of surface, and calculating the average of the center-to-center distances of the micropores obtained from the images of five sites of the surface.

Next, a production method of the cell culture carrier of this invention will be described in detail.

The method of producing the cell culture carrier of this invention is not particularly limited, and as the method thereof, a method of forming a cell culture carrier by performing at least, anodizing treatment (hereinafter, also referred to as "anodizing treatment (A)") in which an oxide film having micropores is formed by anodizing an aluminum substrate, separating treatment (hereinafter, also referred to as "separating treatment (B)") in which the oxide film is separated from the aluminum substrate by removing the aluminum substrate after the anodizing treatment, penetrating treatment (hereinafter, also referred to as "penetrating treatment (C)") in which the micropores of the oxide film separated by the separating treatment are made to penetrate the oxide film, and opening-enlarging treatment (hereinafter, also referred to as "opening-enlarging treatment (D)") in which the opening diameter of the front surface-side opening portion or the rear surface-side opening portion of the micropores which have been penetration-treated by the penetrating treatment is enlarged, in this order; a method of forming a cell culture carrier by performing an opening-forming and enlarging treatment (hereinafter, also referred to as "opening-forming and enlarging treatment (E)") in which the opening diameter of the front surface-side opening portion or the rear surface-side opening portion of the micropores is enlarged simultaneously with making the micropores of the oxide film separated by the separating treatment penetrate after performing the anodizing treatment (A) and the separating treatment (B); or the like can be exemplified.

[Aluminum Substrate]

As the aluminum substrate subjected to each of the treatments which will be described later, those described in paragraphs [0010] to [0012] of JP 2010-226975 A can be used. Thermal treatment, degreasing treatment, and mirror finishing treatment can also be performed in the same manner as each of the treatments described in paragraphs [0013] to [0023] of JP 2010-226975 A.

[Anodizing Treatment (A)]

The anodizing treatment (A) is a treatment in which an oxide film having micropores is formed on the surface of an aluminum substrate by anodizing the aluminum substrate. As the anodizing treatment, conventionally known methods can be used. However, from the viewpoint of arranging the micropores with a high degree of regularity, it is preferable to use self-regularization process or constant voltage treatment.

Herein, the anodizing treatment can be performed in the same manner as each of the treatments described in paragraphs [0024] to [0071] of JP 2010-226975 A.

[Separating Treatment (B)]

The separating treatment (B) is a treatment in which the anodic oxide film is separated from the aluminum substrate by removing the aluminum substrate after the anodizing treatment (A). For removing the aluminum substrate, for example, the aluminum substrate having undergone the anodizing treatment is brought into contact with a treatment solution which dissolves aluminum but does not dissolve alumina, and in this manner, the anodic oxide film from which the aluminum substrate has been removed can be obtained.

Herein, the separating treatment can be performed in the same manner as each of the treatments described in paragraphs [0072] to [0076] of JP 2010-226975 A.

[Penetrating Treatment (C)]

The penetrating treatment (C) is a treatment in which the micropores of the anodic oxide film separated by the separating treatment (B) are made to penetrate the anodic oxide film.

In the penetrating treatment (C), the anodic oxide film is partially dissolved by immersing the anodic oxide film in an acid aqueous solution or an alkali aqueous solution. Thus, the anodic oxide film of the micropore base portion is removed to be penetrated by micropores, whereby micropores having a uniform diameter from the front surface-side opening portion to the rear surface-side opening portion are formed.

Herein, the penetrating treatment can be performed in the same manner as each of the treatments disclosed in paragraphs [0077] to [0081] of JP 2010-226975 A.

[Opening-Enlarging Treatment (D)]

The opening-enlarging treatment (D) is a treatment for enlarging the opening diameter of the front surface-side opening portion or the rear surface-side opening portion of the micropores which have been penetration-treated by the penetrating treatment (C). By the opening-enlarging treatment, it is possible to obtain micropores having a shape in which the average diameter increases or decreases toward the rear surface-side opening portion from the front surface-side opening portion.

In the opening-enlarging treatment, the front surface portion or the rear surface portion of the anodic oxide film obtained by the penetrating treatment is brought into contact with an aqueous acid solution or an aqueous alkali solution. The method of bringing the anodic oxide film into contact with such a solution is not particularly limited, and examples of the method include a dipping method and a spraying method. Between these, the dipping method is preferable.

When the aqueous acid solution is used for the opening-enlarging treatment, it is preferable to use an aqueous solution of an inorganic acid such as sulfuric acid, phosphoric acid, nitric acid, or hydrochloric acid or to use an aqueous solution of a mixture of these acids. The concentration of the aqueous acid solution is preferably 0.1% by mass to 1% by mass, and the temperature of the aqueous acid solution is preferably 15° C. to 30° C.

When the aqueous alkali solution is used for the opening-enlarging treatment, it is preferable to use an aqueous solution of at least one kind of alkali selected from a group consisting of sodium hydroxide, potassium hydroxide, and lithium hydroxide. The concentration of the aqueous alkali solution is preferably 0.01% by mass to 1% by mass, and the temperature of the aqueous alkali solution is preferably 15° C. to 30° C.

The anodic oxide film is dipped in the aqueous acid solution or the aqueous alkali solution, preferably for 0.5 minutes to 30 minutes, more preferably for 1 minute to 25 minutes, and even more preferably for 3 minutes to 20 minutes.

[Opening-Forming and Enlarging Treatment (E)]

The opening-forming and enlarging treatment (E) is a treatment for enlarging the opening diameter of the front surface-side opening portion or the rear surface-side opening portion of the micropores simultaneously with making the micropores of the anodic oxide film separated by the separating treatment (B) penetrate. By the opening-forming and enlarging treatment, it is possible to obtain micropores having a shape in which the average diameter increases or decreases toward the rear surface-side opening portion from the front surface-side opening portion.

In the opening-forming and enlarging treatment, by bringing the anodic oxide film obtained by the separating treatment into contact with an acid aqueous solution or an alkali aqueous solution, the anodic oxide film is partially dissolved.

Herein, since the opening-forming and enlarging treatment is a treatment performed in place of the penetrating treatment (C) and the opening-enlarging treatment (D) described above, it is preferable to use an acid aqueous solution or an alkali aqueous solution at a higher temperature compared to the penetrating treatment (C). By doing so, it is possible to reliably enlarge the opening diameter of the front surface-side opening portion or the rear surface-side opening portion of the micropores simultaneously with making the micropores penetrate by removing the anodic oxide film of the micropore base portion.

In a case of using an acid aqueous solution in the opening-forming and enlarging treatment, it is preferable to use an aqueous solution of an inorganic acid such as sulfuric acid, phosphoric acid, nitric acid, or hydrochloric acid, or to use an aqueous solution of a mixture of these acids. The concentration of the acid aqueous solution is preferably 1% by mass to 10% by mass. The temperature of the acid aqueous solution is preferably 41° C. to 50° C.

In a case of using an alkali aqueous solution in the opening-forming and enlarging treatment, it is preferable to use an aqueous solution of at least one kind of alkali selected from a group consisting of sodium hydroxide, potassium hydroxide and lithium hydroxide. The concentration of the alkali aqueous solution is preferably 0.1% by mass to 5% by mass. The temperature of the alkali aqueous solution is preferably 36° C. to 45° C.

Specifically, a phosphoric acid aqueous solution of 50 g/L and 45° C., a sodium hydroxide aqueous solution of 0.5 g/L and 42° C., or a potassium hydroxide aqueous solution of 0.5 g/L and 42° C. can be suitably used.

The time of immersion in an acid aqueous solution or an alkali aqueous solution is preferably 15 seconds to 175 seconds, more preferably 20 seconds to 160 seconds, and even more preferably 30 seconds to 150 seconds.

After the opening-forming and enlarging treatment, the anodic oxide film is subjected to washing treatment with water. In order to suppress change of the opening diameter of the micropores due to hydration, the washing treatment with water is preferably performed at 30° C. or lower.

In addition, between the separating treatment and the opening-forming and enlarging treatment, or, at any time after the opening-forming and enlarging treatment, it is also possible to perform a heat treatment of heating the oxide film formed by the anodizing treatment for at least 10 minutes at a temperature of 50° C. or higher.

Hereinafter, the cell culture vessel of this invention will be described in detail.

[Cell Culture Vessel]

The cell culture vessel of this invention is a cell culture vessel including at least one culture well that has a culture chamber accommodating a cell culture medium and the aforementioned cell culture carrier that has a front surface, to which cells adhere, positioned inside the culture chamber and is disposed such that the cell culture medium fills the cell culture carrier from the front surface to the rear surface of the cell culture carrier.

Figure 4:
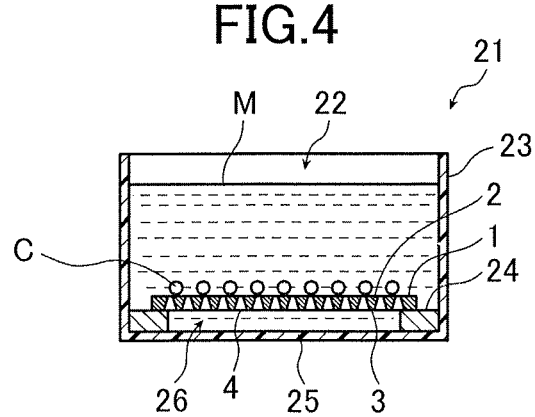
FIG. 4 is a cross-sectional view showing an example of a preferable embodiment of the cell culture vessel of this invention.

FIG. 4 is a schematic cross-sectional view showing an example of a preferable embodiment of a cell culture vessel 21 of this invention.

The cell culture vessel 21 has the shape of a cylinder of which the top is opened. The cell culture vessel 21 includes a culture well 23 that has a culture chamber 22 accommodating a cell culture medium M inside the chamber, and the cell culture carrier 1 that is disposed such that the front surface 2 and the rear surface 3 are positioned inside the culture chamber 22. A cylindrical supporter 24 is disposed inside the culture chamber 22. The supporter 24 supports the cell culture carrier 1 from below, and accordingly, a gap 26 filled with the cell culture medium M is formed between the rear surface 3 of the cell culture carrier 1 and a bottom plate 25 of the culture chamber 22.

Thus, when the cell culture carrier 1 has the plurality of micropores 4, the cell culture medium M can be brought into contact with the cells C which are cultured in a state of adhering on the front surface 2 of the cell culture carrier 1 from not only the upper side but also the lower side, and the growth of the cells C can be accelerated. In addition, as described above, since the plurality of micropores 4 has a shape in which the average diameter gradually increases or decreases toward the rear surface-side opening portion 6 from the front surface-side opening portion 5, it is possible to allow the cell culture medium M to effectively flow between the front surface 2 side and the rear surface 3 side, and it is possible to greatly improve the viability of the cell.

Moreover, the cell culture vessel of this invention can be configured such that the vessel further includes an accommodation portion that has an accommodation chamber accommodating the cell culture medium in an amount greater than that of the cell culture medium accommodated in the culture chamber; the cell culture carrier configures at least a portion of the bottom plate of the culture well; the culture well is disposed such that the bottom plate is positioned inside the accommodation chamber; and the culture chamber is in communication with the accommodation chamber through the plurality of micropores.

Figure 5:
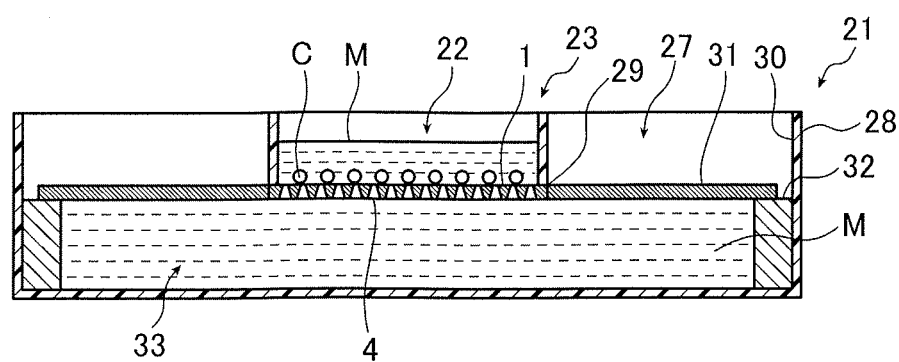
FIG. 5 is a cross-sectional view showing a modification example of the cell culture vessel of this invention.

For example, as shown in FIG. 5, the cell culture vessel can includes the culture well 23 that has the shape of a cylinder of which the top is opened, the bottom plate configured with the aforementioned cell culture carrier 1, and the culture chamber 22 accommodating the cell culture medium M inside the chamber; and an accommodation portion 28 that has the shape of a cylinder of which the top is opened and an accommodation chamber 27 accommodating the cell culture medium M, which is in an amount greater than that of the cell culture medium M accommodated in the culture chamber 22 of the culture well 23, inside the chamber. In this vessel, the culture well 23 can be positioned inside the accommodation chamber 27 of the accommodation portion 28. The culture well 23 has an expansion portion 31 which is in the form of a disc extending toward a side 30 of the accommodation portion 28 from a side edge portion 29 of the cell culture carrier 1. The accommodation portion 28 has a supporter 32, which supports the expansion portion 31 from below, inside the accommodation chamber 27. Consequentially, a gap 33 is formed between the bottom surface of the accommodation portion 28 and the rear surface 3 of the cell culture carrier 1, and the cell culture medium M accommodated in the accommodation chamber 27 can fill the gap 33. The culture chamber 22 of the culture well 23 is in communication with the accommodation chamber 27 of the accommodation portion 28 through the plurality of micropores 4. Therefore, the cell culture medium M accommodated in the culture chamber 22 and the cell culture medium M accommodated in the accommodation chamber 27 can be exchanged with each other through the plurality of micropores 4.

Figure 6:
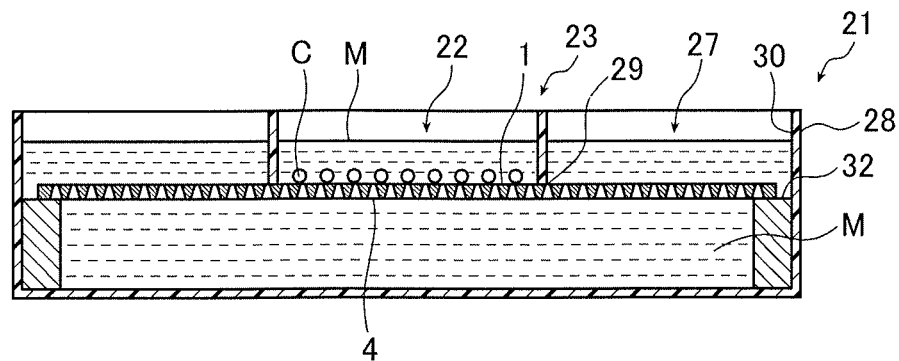
FIG. 6 is a cross-sectional view showing another modification example of the cell culture vessel of this invention.

Furthermore, as shown in FIG. 6, it is preferable for the expansion portion 31 to be formed of an anodic oxide film having a plurality of micropores penetrating the film in the thickness direction and to be disposed in the vessel integrally with the cell culture carrier 1. That is, it is preferable for the bottom plate 25 and expansion portion 31 of the culture well 23 to be configured with the aforementioned cell culture carrier 1.

As described above, the plurality of micropores 4 has a shape in which the average diameter gradually increases or decreases toward the rear surface-side opening portion 6 from the front surface-side opening portion 5. Accordingly, it is possible to allow the cell culture medium M to effectively flow between the culture chamber 22 side and the accommodation chamber 27 side. It is generally known that during cell culturing, due to lactic acid and the like generated from the cell C cultured, the cell culture medium M deteriorates, and this leads to decrease in viability of the cell C. In the cell culture vessel 21 of this invention, the cell culture medium M effectively flows between the culture chamber 22 side and the accommodation chamber 27 side such that the cell culture medium M is sequentially changed around the cell C cultured on the front surface 2 of the cell culture carrier 1. Therefore, the viability of the cell C can be greatly increased.

Moreover, generally, during cell culturing, in order to prevent the cell viability from greatly decreasing due to marked deterioration of the cell culture medium M, the cell culture medium M in the culture chamber 22 needs to be periodically replaced. In the cell culture vessel 21 of this invention, the amount of the cell culture medium M flowing to the culture chamber 22 and the accommodation chamber 27 is increased, and accordingly, deterioration of the cell culture medium M accommodated in the culture chamber 22 is inhibited. Therefore, the number of times the cell culture medium M is replaced can be reduced. Furthermore, as described in the cell culture medium-replacing method which will be described later, it is possible to replace the cell culture medium M while reducing a load applied to the cell C, and as a result, decrease in the cell viability can be further inhibited.

The cells cultured in the cell culture vessel of this invention are not particularly limited, and for example, it is possible to use normal cells such as mesenchymal cells, hepatocytes, fibroblasts, endothelial cells, nerve cells, myocardial cells, glial cells, corneal epithelial cells, chondrocytes, osteoblasts, and adipocytes. It is also possible to use abnormal cells such as cancer-derived cell strains (for example, HepG2 and HuH-7), immortalized cells (for example, HHY41, NKNT-3, and Fa2N-4 strains), and cells showing chromosomal aberration. Moreover, iPS cells, ES cells, and the like can be used.

As the cell culture medium used in the cell culture vessel of this invention, it is possible to use a cell culture medium appropriately prepared according to the type of cell to be cultured.

Hereinafter, regarding the cell culture vessel of this invention shown in FIG. 6, a cell culture medium-replacing method will be described in detail.

Figure 7A:
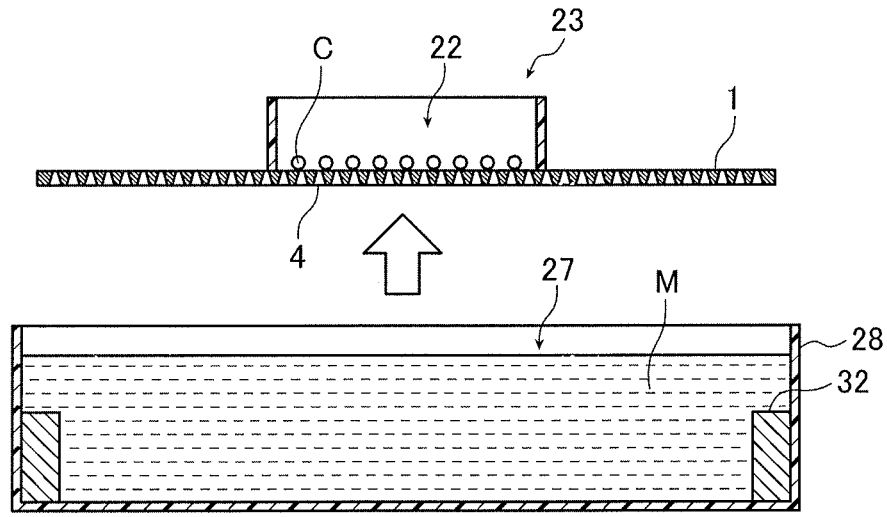
FIGS. 7A to 7C are cross-sectional views showing an example of a method of replacing a cell culture medium of the cell culture vessel.

First, when the cell C is cultured in the state shown in FIG. 6, and the cell culture medium M deteriorates, as shown in FIG. 7A, the culture well 23 is taken out of the accommodation chamber 27 of the accommodation portion 28. At this time, the cell culture medium M in the culture chamber 22 flows into the accommodation chamber 27 through the plurality of micropores 4 of the cell culture carrier 1 configuring the bottom plate of the culture well 23. That is, the entirety of the cell culture medium M in the cell culture vessel 21 is accommodated in the accommodation chamber 27.

Figure 7B:
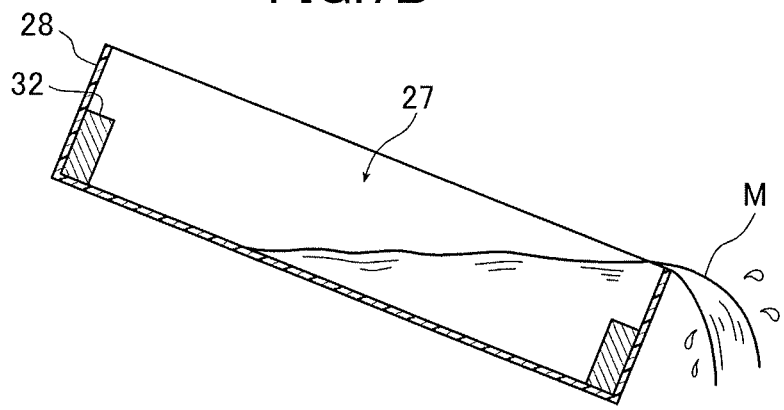
Figure 7C:
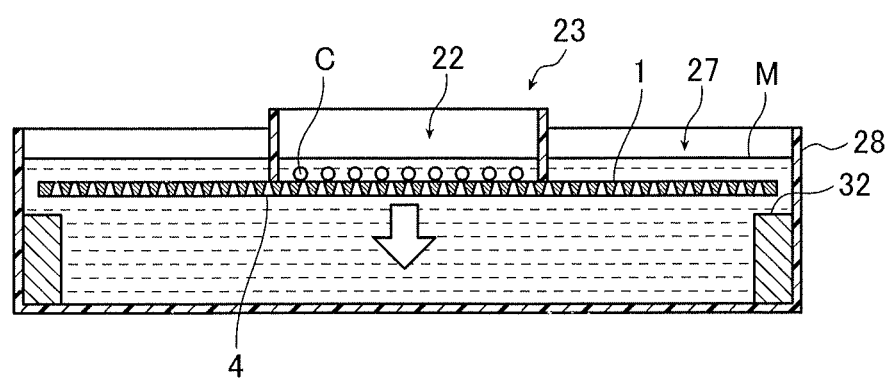

Subsequently, as shown in FIG. 7B, after the cell culture medium M having been accommodated in the accommodation chamber 27 is removed, a new cell culture medium M is supplied into the accommodation chamber 27. Thereafter, as shown in FIG. 7C, the culture well 23 is accommodated in the accommodation chamber 27 of the accommodation portion 28. At this time, as the culture well 23 gradually sinks into the cell culture medium M of the accommodation chamber 27, the cell culture medium M flows into the culture chamber 22 from the accommodation chamber 27 through the plurality of micropores 4 of the cell culture carrier 1, and at a point in time when the culture well 23 comes into contact with the supporter 32, the culture chamber 22 is filled with the cell culture medium M.

It is generally known that when the cell culture medium M in the culture chamber 22 is replaced using a tool such as a pipette, the cell culture medium M is powerfully supplied from the pipette, or alternatively, the tip of the pipette comes into direct contact with the cell, and consequentially, the cell C is damaged, and viability of the cell C decreases. In the cell culture vessel of this invention shown in FIG. 6, as described above, it is possible to calmly replace the cell culture medium M in the culture chamber 22 without using a tool such as a pipette, and accordingly, decrease in the viability of the cell C can be inhibited. In the cell culture vessel shown in FIG. 5, the cell culture medium M can be replaced in the same manner as above, and accordingly, decrease in the viability of the cell C can be inhibited.

Figure 8:
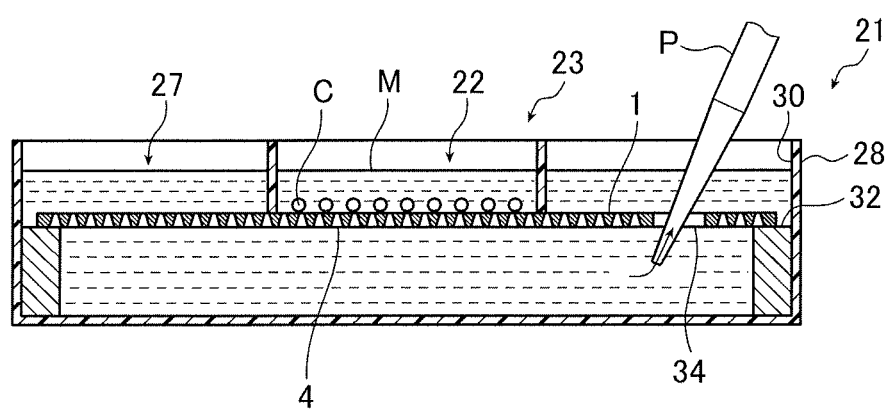
FIG. 8 is a cross-sectional view showing a modification example of the method of replacing a cell culture medium of the cell culture vessel.

As shown in FIG. 8, in a portion of the cell culture carrier 1 configuring the expansion portion of the culture well 23, an insertion hole 34 for inserting a pipette P may be formed, such that the cell culture medium M accommodated in the accommodation chamber 27 can be replaced through the insertion hole 34, and at the same time, the cell culture medium M accommodated in the culture chamber 22 can be replaced.

As described above, since the pipette P is not directly inserted into the culture chamber 22, it is possible to calmly replace the cell culture medium M.

EXAMPLES

Hereinafter, this invention will be described specifically based on examples. However, this invention is not limited to the examples.

Example 1

(1) Electrolytic Polishing Treatment

A high-purity aluminum substrate (manufactured by Sumitomo Light Metal Industries, Ltd., purity of 99.999% by mass, thickness of 0.4 mm) was cut into an area of 10 cm×10 cm and subjected to electrolytic polishing treatment by using an electrolytic polishing solution having the following composition, under conditions of a voltage of 10 V and a solution temperature of 65° C. A carbon electrode was used as a cathode, and GP-250-30R (manufactured by TAKASAGO LTD.) was used as a power source.

(Composition of Electrolytic Polishing Solution)

| | |
|---|---|
| 85% by mass phosphoric acid (reagent manufactured by Wako Pure Chemical Industries, Ltd.) | 1,320 mL |

| | |
|---|---|
| Pure water | 80 mL |
| Sulfuric acid | 600 mL |

(2) Anodizing Treatment

A sample obtained after the electrolytic polishing treatment performed as above was subjected to anodizing treatment for 25 minutes by using an electrolytic solution of 0.50 mol/L oxalic acid, and under conditions of a voltage of 40.0 V, a solution temperature of 15° C., and a solution flow rate of 3.0 m/min. Moreover, the sample obtained after the anodizing treatment was subjected to film-removing treatment in which the sample was dipped in an aqueous mixed solution of 0.5 mol/L phosphoric acid for 20 minutes at 40° C. This treatment was repeated 4 times.

Furthermore, the sample was subjected to re-anodizing treatment for 15 hours by using an electrolytic solution of 0.5 mol/L oxalic acid, and under re-anodizing treatment conditions of a voltage of 41.7 V, a solution temperature of 15° C., and a solution flow rate of 3.0 m/min. In addition, the sample was subjected to the film-removing treatment in which the sample was immersed in an aqueous mixed solution of 0.5 mol/L phosphoric acid for 21 minutes at 40° C. As a result, on the surface of the aluminum substrate, an anodic oxide film in which straight tube-like micropores were arranged in the form of honeycomb was formed.

In both the anodizing treatment and re-anodizing treatment, a stainless steel electrode was used as a cathode, and GP0110-30R (manufactured by TAKASAGO LTD.) was used as a power source. In addition, NeoCool BD36 (manufactured by YAMATO SCIENTIFIC CO., LTD.) was used as a cooling apparatus, and Pair Stirrer PS-100 (manufactured by EYELA TOKYO RIKAKIKAI CO., LTD.) was used as a stirring and heating apparatus.

(3) Separating Treatment

The sample obtained after the anodizing treatment performed as above was immersed in an aqueous mixed solution consisting essentially of 20% by mass hydrochloric acid and 0.1 mol/L cupric chloride, for 20 minutes at 10° C. In this manner, the aluminum substrate was dissolved and removed, and a microstructure formed of an anodic oxide film having micropores was prepared.

(4) Opening-Forming and Enlarging Treatment

The sample after the separating treatment obtained as described above was washed with wash water. Then, the base portion of the anodic oxide film was removed by immersing only the barrier layer side in 0.1 M KOH at 42° C. for 30 seconds, whereby a cell culture carrier formed of the anodic oxide film having micropores of which the rear surface opening diameter was enlarged was prepared.

<Shape Analysis of Cell Culture Carrier>

For the cell culture carrier obtained after the opening-forming and enlarging treatment performed as above, images (20,000× magnification) of five sites of the front surface and rear surface of the cell culture carrier and images (20,000× magnification) of cross-section of five sites of the cell culture carrier were captured by FE-SEM.

The average opening diameter A was obtained by measuring the diameter of all of the micropores present in a field of view of 1 µm×1 µm in the images of five sites of the front surface and calculating the average thereof.

The average opening diameter B was obtained by measuring the diameter of all of the micropores present in a field of view of 1 µm×1 µm in the images of five sites of the rear surface and calculating the average thereof.

The center-to-center distance was obtained by measuring the center-to-center diameter of all of the micropores present in a field of view of 1 µm×1 µm in the images of five sites of the front surface and the images of five sites of the rear surface, and calculating the average thereof.

Herein, the front surface refers to a surface on which the opening-forming and enlarging treatment was not performed, and the rear surface refers to a surface on which the opening diameter was enlarged by performing the opening-forming and enlarging treatment.

Thickness of cell culture carrier: 150 µm
Depth of micropores: 150 µm
Average opening diameter A of front surface: 50 nm
Average opening diameter B of rear surface: 68 nm
Center-to-center distance of micropores: 100 nm (5) Sterilizing Treatment The cell culture carrier obtained as above was subjected to sterilizing treatment in which ultrasonic cleaning was performed for 5 minutes on the cell culture carrier by using ethanol, and then the cell culture carrier was dried in an oven.

(6) Cell Culturing Process

After the sterilization, cells were cultured using the cell culture carrier cooled to room temperature.

(a) Used cells: BAE (Bovine Aortic Endothelial cells)
(b) Used culture medium: Eagle minimum medium, 10% fetal bovine serum
(c) Pretreatment: A petri dish having a height of 10 mm and an inner diameter of 35 mm was prepared, and a cylindrical supporter configured with polystyrene that had a thickness of 1 mm, an outer diameter of 35 mm, and a height of 5 mm was disposed in the petri dish. Thereafter, the cell culture medium was filled in the petri dish up to a height of 8 mm, and then the cell culture carrier was sunk into the cell culture medium and disposed on the supporter. Subsequently, on the front surface of the cell culture carrier, a side of the culture well 23 configured with polystyrene that had a thickness of 1 mm, an outer diameter of 10 mm, and a height of 5 mm was disposed.

(d) Cell seeding: Cells that had been cultured beforehand were collected by trypsin treatment, and the cell concentration was regulated to be 40,000 cells/mL. After the medium in the culture chamber of the culture well was discarded, a cell sap of which the cell count had been beforehand regulated to be 7,000 cells/cm$^2$ was seeded into the culture chamber.

(e) Culturing: The cells were cultured for 3 days at 37° C. by using a $CO_2$ incubator.

Example 2

A cell culture carrier was prepared in the same manner as in Example 1 except that the above-described (2) Anodizing treatment and (4) Opening-forming and enlarging treatment were performed by a method described below, and cell culturing was performed.

(2) Anodizing Treatment

The sample after the electrolytic polishing treatment was subjected to the anodizing treatment for 25 minutes by using an electrolytic solution of 0.50 mol/L oxalic acid, and under conditions of a voltage of 40.0 V, a solution temperature of 15° C., and a solution flow rate of 3.0 m/min. The sample after the anodizing treatment was further subjected to film-removing treatment in which the sample was immersed in a mixed aqueous solution of 0.5 mol/L phosphoric acid for 20 minutes under the condition of 40° C. This treatment was repeated four times.

Furthermore, the sample was subjected to re-anodizing treatment for 15 hours by using an electrolytic solution of 0.5 mol/L oxalic acid, and under re-anodizing treatment conditions of a voltage of 41.7 V, a solution temperature of 15° C., and a solution flow rate of 3.0 m/min. In addition, the sample was subjected to the film-removing treatment in which the sample was immersed in an aqueous mixed solution of 0.5 mol/L phosphoric acid for 23 minutes at 40° C. As a result, on the surface of the aluminum substrate, an anodic oxide film in which straight tube-like micropores were arranged in the form of honeycomb was formed.

(4) Opening Forming and Enlarging Treatment

The sample after the separating treatment obtained described above was washed with wash water. Then, the base portion of the anodic oxide film was removed by immersing only the barrier layer side in 0.1 M KOH at 42° C. for 40 seconds, whereby a cell culture carrier formed of the anodic oxide film having micropores of which the rear surface opening diameter was enlarged was prepared. The results obtained by checking the shape of the cell culture carrier are shown below.

Thickness of cell culture carrier: 150 μm
Depth of micropores: 150 μm
Average opening diameter A of front surface: 60 nm
Average opening diameter B of rear surface: 75 nm
Center-to-center distance of micropores: 100 nm Example 3

A cell culture carrier was prepared in the same manner as in Example 1 except that the above-described (2) Anodizing treatment and (4) Opening-forming and enlarging treatment were performed by a method described below, and cell culturing was performed.

(2) Anodizing Treatment

The sample after the electrolytic polishing treatment was subjected to the anodizing treatment for 25 minutes by using an electrolytic solution of 0.50 mol/L oxalic acid, and under conditions of a voltage of 40.0 V, a solution temperature of 15° C., and a solution flow rate of 3.0 m/min. The sample after the anodizing treatment was further subjected to film-removing treatment in which the sample was immersed in a mixed aqueous solution of 0.5 mol/L phosphoric acid for 20 minutes under the condition of 40° C. This treatment was repeated four times.

Furthermore, the sample was subjected to re-anodizing treatment for 15 hours by using an electrolytic solution of 0.5 mol/L oxalic acid, and under re-anodizing treatment conditions of a voltage of 41.7 V, a solution temperature of 15° C., and a solution flow rate of 3.0 m/min. In addition, the sample was subjected to the film-removing treatment in which the sample was immersed in an aqueous mixed solution of 0.5 mol/L phosphoric acid for 23 minutes at 40° C. As a result, on the surface of the aluminum substrate, an anodic oxide film in which straight tube-like micropores were arranged in the form of honeycomb was formed.

(4) Opening Forming and Enlarging Treatment

The sample after the separating treatment obtained described above was washed with wash water. Then, the base portion of the anodic oxide film was removed by immersing only the barrier layer side in 0.1 M KOH at 42° C. for 50 seconds, whereby a cell culture carrier formed of the anodic oxide film having micropores of which the rear surface opening diameter was enlarged was prepared. The results obtained by checking the shape of the cell culture carrier are shown below.

Thickness of cell culture carrier: 150 μm
Depth of micropores: 150 μm
Average opening diameter A of front surface: 68 nm
Average opening diameter B of rear surface: 81 nm
Center-to-center distance of micropores: 100 nm Example 4

A cell culture carrier was prepared in the same manner as in Example 3. Subsequently, cell culturing was performed in the same manner as in Example 3 except that in (6) Cell culturing process, the obtained cell culture carrier was reversely installed in the petri dish in contrast to Example 3. The results obtained by checking the shape of the cell culture carrier are shown below.

Thickness of cell culture carrier: 150 μm
Depth of micropores: 150 μm
Average opening diameter A of front surface: 81 nm
Average opening diameter B of rear surface: 68 nm
Center-to-center distance of micropores: 100 nm Example 5

A cell culture carrier was prepared in the same manner as in Example 1 except that the above-described (2) Anodizing treatment and (4) Opening-forming and enlarging treatment were performed by a method described below, and cell culturing was performed.

(2) Anodizing Treatment

The sample after the electrolytic polishing treatment was subjected to the anodizing treatment for 25 minutes by using an electrolytic solution of 0.50 mol/L oxalic acid, and under conditions of a voltage of 40.0 V, a solution temperature of 15° C., and a solution flow rate of 3.0 m/min. The sample after the anodizing treatment was further subjected to film-removing treatment in which the sample was immersed in a mixed aqueous solution of 0.5 mol/L phosphoric acid for 20 minutes under the condition of 40° C. This treatment was repeated four times.

Furthermore, the sample was subjected to re-anodizing treatment for 15 hours by using an electrolytic solution of 0.5 mol/L oxalic acid, and under re-anodizing treatment conditions of a voltage of 41.7 V, a solution temperature of 15° C., and a solution flow rate of 3.0 m/min. In addition, the sample was subjected to the film-removing treatment in which the sample was immersed in an aqueous mixed solution of 0.5 mol/L phosphoric acid for 25 minutes at 40° C. As a result, on the surface of the aluminum substrate, an anodic oxide film in which straight tube-like micropores were arranged in the form of honeycomb was formed.

(4) Opening Forming and Enlarging Treatment

The sample after the separating treatment obtained described above was washed with wash water. Then, the base portion of the anodic oxide film was removed by immersing only the barrier layer side in 0.1 M KOH at 42° C. for 60 seconds, whereby a cell culture carrier formed of the anodic oxide film having micropores of which the rear surface opening diameter was enlarged was prepared. The results obtained by checking the shape of the cell culture carrier are shown below.

Thickness of cell culture carrier: 150 μm
Depth of micropores: 150 μm
Average opening diameter A of front surface: 78 nm
Average opening diameter B of rear surface: 90 nm
Center-to-center distance of micropores: 100 nm Example 6

A cell culture carrier was prepared in the same manner as in Example 3. Thereafter, cells were cultured in the same manner as in Example 3, except that the cells and culture medium used in the cell culturing process were changed as below.
(a) Used cells: rat hepatocytes
(b) Used culture medium: DMEM medium Example 7

A cell culture carrier was prepared in the same manner as in Example 3. Thereafter, cells were cultured in the same manner as in Example 3, except that the cells and culture medium used in the cell culturing process were changed as below.
(a) Used cells: HepG2 cells (human embryoma-derived cells)
(b) Used culture medium: William's E medium, 10% fetal bovine serum Example 8

A cell culture carrier was prepared in the same manner as in Example 3. Thereafter, cells were cultured in the same manner as in Example 3, except that the cells and culture medium used in the cell culturing process were changed as below.
(a) Used cells: HuH7 cells (human hepatoma-derived cells)
(b) Used culture medium: William's E medium, 10% fetal bovine serum Example 9

A cell culture carrier was prepared in the same manner as in Example 3. Thereafter, cells were cultured in the same manner as in Example 3, except that the cells and culture medium used in the cell culturing process were changed as below.
(a) Used cells: RIN-5F cells (rat Langerhans islet-derived cells)
(b) Used culture medium: RPMI-1640 medium, 10% fetal bovine serum Example 10

A cell culture carrier was prepared in the same manner as in Example 3. Thereafter, cells were cultured in the same manner as in Example 3, except that the cells and culture medium used in the cell culturing process were changed as below.
(a) Used cells: 129SV cells (mouse ES cells)
(b) Used culture medium: medium for ES cells Example 11

A cell culture carrier was prepared in the same manner as in Example 1 except that the above-described (2) Anodizing treatment and (4) Opening-forming and enlarging treatment were performed by a method described below, and cell culturing was performed.
(2) Anodizing Treatment
The sample after the electrolytic polishing treatment was subjected to the anodizing treatment for 25 minutes by using an electrolytic solution of 0.50 mol/L oxalic acid, and under conditions of a voltage of 40.0 V, a solution temperature of 15° C., and a solution flow rate of 3.0 m/min. The sample after the anodizing treatment was further subjected to film-removing treatment in which the sample was immersed in a mixed aqueous solution of 0.5 mol/L phosphoric acid for 20 minutes under the condition of 40° C. This treatment was repeated four times.

Furthermore, the sample was subjected to re-anodizing treatment for 15 hours by using an electrolytic solution of 0.5 mol/L oxalic acid, and under re-anodizing treatment conditions of a voltage of 41.7 V, a solution temperature of 15° C., and a solution flow rate of 3.0 m/min. In addition, the sample was subjected to the film-removing treatment in which the sample was immersed in an aqueous mixed solution of 0.5 mol/L phosphoric acid for 24 minutes at 40° C. As a result, on the surface of the aluminum substrate, an anodic oxide film in which straight tube-like micropores were arranged in the form of honeycomb was formed.

(4) Opening Forming and Enlarging Treatment
The sample after the separating treatment obtained described above was washed with wash water. Then, the base portion of the anodic oxide film was removed by immersing only the barrier layer side in 0.1 M KOH at 42° C. for 45 seconds, whereby a cell culture carrier formed of the anodic oxide film having micropores of which the rear surface opening diameter was enlarged was prepared. The results obtained by checking the shape of the cell culture carrier are shown below.
Thickness of cell culture carrier: 150 μm
Depth of micropores: 150 μm
Average opening diameter A of front surface: 71 nm
Average opening diameter B of rear surface: 78 nm
Center-to-center distance of micropores: 100 nm Comparative Example 1

A cell culture carrier was prepared as below, with reference to the preparation method for membrane 2 described in paragraph [0104] of JP 2010-226975 A and the preparation method of Comparative example 1 described in paragraph [0127] of the same document.
(1) Electrolytic Polishing Treatment
Electrolytic polishing treatment was performed in the same manner as in Example 1, except that a high-purity aluminum substrate having purity of 99.99% by mass was used.
(2) Anodizing Treatment
A sample obtained after the electrolytic polishing treatment performed as above was subjected to anodizing treatment for 2.5 hours by using an electrolytic solution of 0.50 mol/L oxalic acid, and under conditions of a voltage of 40.0 V, a solution temperature of 15° C., and a solution flow rate of 3.0 m/min. Moreover, the sample obtained after the anodizing treatment was subjected to film-removing treatment in which the sample was dipped in an aqueous mixed solution of 0.5 mol/L phosphoric acid for 20 minutes at 40° C. This treatment was repeated 4 times.

Furthermore, the sample was subjected to re-anodizing treatment for 10 hours by using an electrolytic solution of 0.5 mol/L oxalic acid, and under re-anodizing treatment conditions of a voltage of 41.7 V, a solution temperature of 15° C., and a solution flow rate of 3.0 m/min. In addition, the sample was subjected to the film-removing treatment in which the sample was immersed in an aqueous mixed solution of 0.5 mol/L phosphoric acid for 20 minutes at 40° C. As a result, on the surface of the aluminum substrate, an anodic oxide film in which straight tube-like micropores were arranged in the form of honeycomb was formed.
(3) Separating Treatment
Separating treatment was performed in the same manner as in Example 1.

(4) Penetrating Treatment

The sample obtained after the separating treatment performed as above was immersed in a KCl solution as a pH buffer solution for 10 minutes such that the KCl solution sufficiently flowed into the micropores. Thereafter, only the side of a barrier layer was immersed in 0.1 M KOH for 4 minutes at 30° C. so as to remove the bottom portion of the anodic oxide film, thereby preparing a cell culture carrier formed of an anodic oxide film having micropores of which the diameter is consistent from the front surface-side opening portion to the rear surface-side opening portion.

Paragraph [0104] of JP 2010-226975 A describes "only the side of a barrier layer was immersed in 0.1 M KOH for 45 minutes at 30° C. so as to remove the bottom portion of the anodic oxide film" in (4) Process of removing aluminum and performing penetrating treatment. However, the time taken for such treatment is considered to be too long to obtain the shape of a microstructure checked by capturing images (for example, a microstructure having an average opening diameter of through holes of 30 nm). Actually, when the sample obtained after the separating treatment was immersed in 0.1 M KOH for 45 minutes at 30° C., most of the sample was dissolved. Therefore, the description of JP 2010-226975 A is considered to be an erroneous description which may be corrected to "immersed in 0.1 M KOH for 4 minutes at 30° C.".

The results obtained by checking the shape of the cell culture carrier are shown below.

Thickness of cell culture carrier: 100 μm
Depth of micropores: 100 μm
Average opening diameter A of front surface: 30 nm
Average opening diameter B of rear surface: 30 nm
Center-to-center distance of micropores: 100 nm
(6) Cell Culturing Process
Cells were cultured in the same manner as in Example 1.

Comparative Example 2

A cell culture carrier was prepared in the same manner as in Comparative example 1 except that the above-described (2) Anodizing treatment and (4) Penetrating treatment were performed by a method described below, and cell culturing was performed.

(2) Anodizing Treatment

The sample after the electrolytic polishing treatment was subjected to the anodizing treatment for 25 minutes by using an electrolytic solution of 0.50 mol/L oxalic acid, and under conditions of a voltage of 40.0 V, a solution temperature of 15° C., and a solution flow rate of 3.0 m/min. The sample after the anodizing treatment was further subjected to film-removing treatment in which the sample was immersed in a mixed aqueous solution of 0.5 mol/L phosphoric acid for 20 minutes under the condition of 40° C. This treatment was repeated four times.

Furthermore, the sample was subjected to re-anodizing treatment for 15 hours by using an electrolytic solution of 0.5 mol/L oxalic acid, and under re-anodizing treatment conditions of a voltage of 41.7 V, a solution temperature of 15° C., and a solution flow rate of 3.0 m/min. In addition, the sample was subjected to the film-removing treatment in which the sample was immersed in an aqueous mixed solution of 0.5 mol/L phosphoric acid for 20 minutes at 40° C. As a result, on the surface of the aluminum substrate, an anodic oxide film in which straight tube-like micropores were arranged in the form of honeycomb was formed.

(4) Penetrating Treatment

The sample after the separating treatment was immersed in a KCl solution as a pH buffer solution for 10 minutes such that the KCl solution sufficiently flowed into the micropores. Thereafter, only the side of a barrier layer was immersed in 0.1 M KOH for 9 minutes at 25° C. so as to remove the bottom portion of the anodic oxide film, thereby preparing a cell culture carrier formed of an anodic oxide film having micropores of which the diameter is consistent from the front surface-side opening portion to the rear surface-side opening portion. The results obtained by checking the shape of the cell culture carrier are shown below.

Thickness of cell culture carrier: 150 μm
Depth of micropores: 150 μm
Average opening diameter A of front surface: 68 nm
Average opening diameter B of rear surface: 68 nm
Center-to-center distance of micropores: 100 nm Comparative Example 3

A cell culture carrier was prepared in the same manner as in Comparative example 2 except that the above-described (4) Penetrating treatment was performed by a method described below, and cell culturing was performed.

(4) Penetrating Treatment

The sample after the separating treatment was immersed in a KCl solution as a pH buffer solution for 10 minutes such that the KCl solution sufficiently flowed into the micropores. Thereafter, only the side of a barrier layer was immersed in 0.1 M KOH for 10 minutes at 25° C. so as to remove the bottom portion of the anodic oxide film, thereby preparing a cell culture carrier formed of an anodic oxide film having micropores of which the diameter is consistent from the front surface-side opening portion to the rear surface-side opening portion. The results obtained by checking the shape of the cell culture carrier are shown below.

Thickness of cell culture carrier: 150 μm
Depth of micropores: 150 μm
Average opening diameter A of front surface: 75 nm
Average opening diameter B of rear surface: 75 nm
Center-to-center distance of micropores: 100 nm The opening diameter ratio of the prepared cell culture carrier was obtained by calculating the ratio of the large average opening diameter to the small average opening diameter (value of large average opening diameter/value of small average opening diameter). The results are shown in the following Table 1.

The opening ratio of the front surface was obtained as follows. Images of five sites on the front surface of the cell culture carrier were captured by FE-SEM, for a viewing field of 1 μm×1 μm for each of the images obtained, the area of the front surface opening portion and the area of the view range were determined, the opening ratio (=the area of the front surface opening portion/the area of the view range) was calculated, and the average value for the opening ratios at the five sites was calculated. The results are shown in the following Table 1.

The opening ratio of the rear surface was obtained as follows. Images of five sites on the rear surface of the cell culture carrier were captured by FE-SEM, for a viewing field of 1 μm×1 μm for each of the images obtained, the area of the rear surface opening portion and the area of the view range were determined, the opening ratio (=the area of the rear surface opening portion/the area of the view range) was calculated, and the average value for the opening ratios at the five sites was calculated. The results are shown in the following Table 1.

The average opening ratio of both surfaces was obtained by calculating (opening ratio of the front surface+opening ratio of the rear surface)/2. The results are shown in the following Table 1.

(Evaluation Method)

By using an optical microscope, 100 cells were randomly selected, and the number of surviving cells among the selected cells was counted, thereby calculating the cell viability. If the cell viability was equal to or higher than 95%, the cell viability was evaluated to be A; if the cell viability was equal to or higher than 90% but less than 95%, it was evaluated to be B; and if the cell viability was less than 90%, it was evaluated to be C. The results are shown in the following Table 1.

TABLE 1

| | Cell culture carrier | | | | | | |
| --- | --- | --- | --- | --- | --- | --- | --- |
| | Front surface-side opening portion Average opening diameter A (nm) | Rear surface-side opening portion Average opening diameter B (nm) | Ratio of opening diameter (times) | Opening ratio of front surface (%) | Opening ratio of rear surface (%) | Average opening ratio of both surfaces (%) | Cell culturing Type of cell | Evaluation Cell viability (%) |
| Example 1 | 50 | 68 | 1.36 | 23 | 42 | 32 | BAE | B |
| Example 2 | 60 | 75 | 1.25 | 33 | 51 | 42 | BAE | B |
| Example 3 | 68 | 81 | 1.19 | 42 | 60 | 51 | BAE | A |
| Example 4 | 81 | 68 | 1.19 | 60 | 42 | 51 | BAE | A |
| Example 5 | 78 | 90 | 1.15 | 55 | 73 | 64 | BAE | A |
| Example 6 | 68 | 81 | 1.19 | 42 | 60 | 51 | Rat hepatocyte | A |
| Example 7 | 68 | 81 | 1.19 | 42 | 60 | 51 | HePG2 | A |
| Example 8 | 68 | 81 | 1.19 | 42 | 60 | 51 | HuH7 | A |
| Example 9 | 68 | 81 | 1.19 | 42 | 60 | 51 | RIN-5F | A |
| Example 10 | 68 | 81 | 1.19 | 42 | 60 | 51 | 129SV | A |
| Example 11 | 71 | 78 | 1.10 | 46 | 55 | 50 | BAE | B |
| Comparative Example 1 | 30 | 30 | 1.0 | 8 | 8 | 8 | BAE | C |
| Comparative Example 2 | 68 | 68 | 1.0 | 42 | 42 | 42 | BAE | C |
| Comparative Example 3 | 75 | 75 | 1.0 | 51 | 51 | 51 | BAE | C |

From the results shown in Table 1, it was found that in Examples 1 to 11 in which the diameters of the micropores gradually increased or decreased toward the rear surface-side opening from the front surface-side opening portion, the viability of the cells was greatly improved compared to that in Comparative Examples 1 to 3 in which the diameters of the plurality of micropores were uniform in the thickness direction.

In addition, it was found that in Example 3 in which the average opening diameter B was 1.15 or greater times the average opening diameter A, the viability of the cells was greatly improved, though the average opening ratios of both surfaces were close values, compared to that in Example 11 in which the average opening diameter B was less than 1.15 times the average opening diameter A.

Moreover, it was found that in Examples 3 to 5 in which the average opening ratio of both surfaces obtained when combining the front surface and the rear surface of the cell culture carrier was equal to or greater than 51%, the viability of the cells was further improved compared to that in Examples 1 and 2 in which the average opening ratio of both surfaces was less than 51%.

Furthermore, any of Examples 6 to 10 in which different types of cells were cultured exhibited high viability of the cells, and consequentially, it was understood that the viability of the cells can be greatly improved regardless of the type of cells.

What is claimed is:

1. A cell culture carrier comprising an anodic oxide film having a plurality of micropores penetrating in a thickness direction from a front surface to a rear surface,
   wherein a thickness of the cell culture carrier is 10 μm to 300 μm,
   wherein an average opening diameter A of a front surface-side opening portion of the plurality of micropores and an average opening diameter B of a rear surface-side opening portion thereof have different values from each other, and
   the plurality of micropores has a shape in which an average diameter continuously increases or continuously decreases toward the rear surface-side opening portion from the front surface-side opening portion.

2. The cell culture carrier according to claim 1,
   wherein a value of a larger one of the average opening diameter A and the average opening diameter B is 1.05 to 10.0 times a value of a smaller one thereof.

3. The cell culture carrier according to claim 1,
   wherein a smaller one of the average opening diameter A and the average opening diameter B is 40 nm to 80 nm.

4. The cell culture carrier according to claim 1,
   wherein a larger one of the average opening diameter A and the average opening diameter B is 65 nm to 100 nm.

5. The cell culture carrier according to claim 1,
   wherein an opening ratio in one of the front surface and the rear surface which has a smaller one of the average opening diameter A and the average opening diameter B is equal to or greater than 20%.

6. The cell culture carrier according to claim 5,
   wherein an average opening ratio of both the front surface and the rear surface is equal to or greater than 51%.

7. A cell culture vessel comprising:
   at least one culture well having a culture chamber accommodating a cell culture medium; and
   the cell culture carrier according to claim 1 that has a front surface to which cells adhere and which is positioned inside the culture chamber, and that is disposed such that the cell culture medium fills the cell culture carrier from the front surface to the rear surface of the cell culture carrier.

8. The cell culture vessel according to claim 7, wherein the cell culture carrier is disposed such that the front surface and the rear surface thereof are positioned inside the culture chamber.

9. The cell culture vessel according to claim 7, further comprising
an accommodation portion that has an accommodation chamber accommodating the cell culture medium in an amount greater than that of the cell culture medium accommodated in the culture chamber,
wherein the cell culture carrier configures at least a bottom plate of the culture well,
the bottom plate of the culture well is disposed so as to be positioned inside the accommodation chamber, and
the culture chamber is in communication with the accommodation chamber through the plurality of micropores.

10. The cell culture vessel according to claim 9, wherein the culture well has an expansion portion that is in the form of a flat plate extending toward a side portion of the accommodation portion from a side edge of the bottom plate, and the accommodation portion has a supporter that supports the expansion portion in the side portion thereof.

11. The cell culture vessel according to claim 10, wherein the expansion portion is formed of the anodic oxide film of the cell culture carrier having the plurality of micropores penetrating the anodic oxide film in a thickness direction.

12. The cell culture carrier according to claim 1, wherein a value of a larger one of the average opening diameter A and the average opening diameter B is 1.05 to 10.0 times a value of a smaller one therof,
the larger one of the average opening diameter A and the average opening diameter B is 65 nm to 100 nm, and
the smaller one of the average opening diameter A and the average opening diameter B is 40 nm to 80 nm.

13. The cell culture carrier according to claim 12, wherein an opening ratio in one of the front surface and the rear surface which has the smaller one of the average opening diameter A and the average opening diameter B is equal to or greater than 20%, and
an average opening ratio of both the front surface and the rear surface is equal to or greater than 51%.

* * * * *